United States Patent [19]

Matthews

[11] Patent Number: 5,684,204

[45] Date of Patent: Nov. 4, 1997

[54] SULFUR CONTAINING DI-TERT-BUTYLPHENOL COMPOUNDS USEFUL AS ANTI-INFLAMMATORY AGENTS

[75] Inventor: Randall Stryker Matthews, Cincinnati, Ohio

[73] Assignee: The Procter & Gamble Company, Cincinnati, Ohio

[21] Appl. No.: 559,014

[22] Filed: Nov. 15, 1995

[51] Int. Cl.$^6$ .................................................. C07C 317/26
[52] U.S. Cl. ........................... 568/31; 568/37; 568/28
[58] Field of Search ........................................... 568/31, 37

[56] References Cited

U.S. PATENT DOCUMENTS

| | | | |
|---|---|---|---|
| 3,711,544 | 1/1973 | Engelhardt et al. | 260/591 |
| 3,784,701 | 1/1974 | Tomcufcik et al. | |
| 3,862,214 | 1/1975 | Cohen et al. | 260/479 R |
| 3,917,672 | 11/1975 | Schmidt | 260/473 |
| 4,124,725 | 11/1978 | Moore | 424/330 |
| 4,130,666 | 12/1978 | Moore | 424/331 |
| 4,172,082 | 10/1979 | Moore | 549/72 |
| 4,357,345 | 11/1982 | Moore | 424/285 |
| 4,418,074 | 11/1983 | Moore | 424/274 |
| 4,440,784 | 4/1984 | Moore | 424/308 |
| 4,535,165 | 8/1985 | Katsumi et al. | 548/204 |
| 4,677,113 | 6/1987 | Moore | 514/448 |
| 4,708,966 | 11/1987 | Loomans et al. | 514/689 |
| 4,714,776 | 12/1987 | Bell et al. | 562/460 |
| 4,833,155 | 5/1989 | Muchowski et al. | 514/423 |
| 4,968,710 | 11/1990 | Rustad | 514/381 |
| 4,982,006 | 1/1991 | Hudec | 568/322 |
| 5,086,064 | 2/1992 | Capris et al. | 514/365 |
| 5,102,897 | 4/1992 | Boschelli et al. | 514/361 |

FOREIGN PATENT DOCUMENTS

| | | | |
|---|---|---|---|
| 0 212 848 | 3/1987 | European Pat. Off. | C07D 257/04 |
| WO 83/01774 | 5/1983 | WIPO | |
| WO 93/07865 | 4/1993 | WIPO | |

OTHER PUBLICATIONS

Batt, D.G. "5-Lipoxygenase Inhibitors and Their Anti-Inflammatory Activities", *Progress in Medicinal Chemistry*, vol. 29 (1992), pp. 1–15, 45–50.

Segio Thea et al; Journal of Organic Chemistry, 53, 4121–4122 Jan. 29, 1988.

*Primary Examiner*—C. Warren Ivy
*Assistant Examiner*—Sreeni Padmabhan
*Attorney, Agent, or Firm*—Mary Pat McMahon; Karen F. Clark; Jacobus C. Rasser

[57] ABSTRACT

The subject invention relates to compounds having the structure:

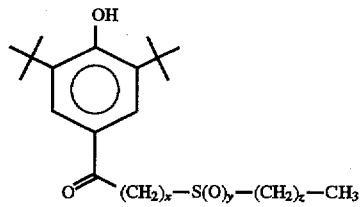

wherein (a) x is from 1 to 5;

(b) y is from 1 to 2; and (c) z is from 0 to 5.

The subject invention also relates to the pharmaceutical compositions comprising the above compounds, and methods of treating inflammation using the compounds.

15 Claims, No Drawings

SULFUR CONTAINING DI-TERT-BUTYLPHENOL COMPOUNDS USEFUL AS ANTI-INFLAMMATORY AGENTS

TECHNICAL FIELD

The subject invention relates to nonsteroidal anti-inflammatory drugs, particularly to substituted sulfur containing di-tert-butylphenol compounds.

BACKGROUND OF THE INVENTION

Di-tert-butylphenol compounds are a class of compounds known for their use as stabilizers for plastics, oils and fats; see, e.g., U.S. Pat. No. 3,711,544 issued to Engelhardt, Fruhstorfer, Hesse, Denttier & Baumer on Jan. 16, 1973.

Certain di-tert-butylphenol compounds and other compounds structurally related thereto have been found to have significant anti-inflammatory and/or analgesic activity. Such compounds, processes for making them, and uses for them are disclosed in the following references: U.S. Pat. Nos. 3,784,701 issued to Tomcufcik, Grassing & Sloboda on Jan. 8, 1974; 3,917,672 issued to Schmidt on Nov. 4, 1975; 4,124,725 issued to Moore on Nov. 7, 1978; 4,130,666 issued to Moore on Dec. 19, 1978; 4,165,383 issued to Moore on Aug. 21, 1979; 4,172,082 issued to Moore on Oct. 23, 1979; 4,357,345 issued to Moore on Nov. 2, 1982; 4,418,074 issued to Moore on Nov. 29, 1983; 4,440,784 issued to Katsumi, Kondo, Yamashita, Hidaka, Hosoe, Ariki, Yamashita & Watanobe on Apr. 3, 1984; 4,535,165 issued to Moore on Aug. 13, 1985; 4,677,113 issued to Bell & Moore on Jun. 30, 1987; 4,708,966 issued to Loomans, Matthews & Miller on Nov. 24, 1987; 4,714,776 issued to Bell & Moore on Dec. 22, 1987; 4,833,155 issued to Muchowski, Greenhouse, Young & Murthy on May 23, 1989; 4,968,710 issued to Rustad on Nov. 6, 1990; 4,982,006 issued to Hudec on Jan. 1, 1991; 5,086,064 issued to Capris, Conner & Sircar on Feb. 4, 1992; 5,102,897 issued to Boschelli, Conner, Kostlan, Kramer, Mullican & Sircar on Apr. 7 1992; European Patent Application No. 0,212,848 of Riker Laboratories, published Mar. 4, 1987; PCT patent application Ser. Nos. WO 83/01774 and WO 83/91775 of Piker Laboratories, both published May 26, 1983; WO 93/07865 of The Procter & Gamble Company, published Apr. 29, 1993; Kaffenberger, R. M., T. H. Eichhold & M. J. Doyle, "Determination of Tebufelone (A New Anti-Inflammatory Drug) Strength and Stability in Bulk Drug, Dosage Formulations and Feed Admixtures by Reversed-Phase High-Performance Liquid Chromatography", *Journal of Chromatography*, Vol. 505 (1990), pp. 349–356. Such compounds are also disclosed and reviewed in Batt, D. G., "5-Lipoxygenase Inhibitors and Their Anti-inflammatory Activities", *Progress in Medicinal Chemistry*, Vol. 29 (1992), pp. 1–15, 45–50, and references disclosed therein.

Although a number of di-tert-butylphenol compounds have been demonstrated to exhibit anti-inflammatory activity, many such compounds exhibit little or no anti-inflammatory activity. Thus it is generally not possible to predict whether such compounds have substantial anti-inflammatory activity without testing for the activity.

It is an object of the subject invention to provide compounds which have effective anti-inflammatory, analgesic and/or anti-oxidant activity.

It is a further object of the subject invention to provide such compounds which cause few adverse side effects.

It is yet another object of the subject invention to provide such compounds which exhibit gastroprotective effects.

It is also an object of the subject invention to provide methods for treating intimation and/or pain using the subject compounds.

SUMMARY OF THE INVENTION

The subject invention involves compounds having the structure:

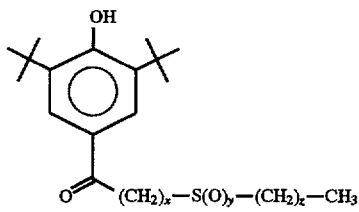

wherein
(a) x is from 1 to 5;
(b) y is from 1 to 2; and
(c) z is from 0 to 5.

Preferably x is from 1 to 3; more preferably from 1 to 2. Preferably z is from 0 to 2; more preferably from 0 to 1. When x is 1 and z is 1, y is preferably 2.

DETAILED DESCRIPTION OF THE INVENTION

As used herein, "alkyl" means a saturated hydrocarbon substituent, straight, branched or cyclic chain, unsubstituted or substituted. Preferred alkyl are C1 to C12; more preferred are C1–C6; more preferred still are C1–C3; especially preferred are C2 and C1.

As used herein, "alkanyl" means a saturated alkyl.

As used herein, "alkanoxy" means a substituent having the structure Q—O—, where Q is alkanyl.

As used herein, "alkanylthiol" means a substituent having the structure Q—S—, where Q is alkanyl.

As used herein, "halo" means fluoro, chloro, bromo or iodo.

Compounds

The subject invention involves particular di-tert-butylphenol compounds having the following structure:

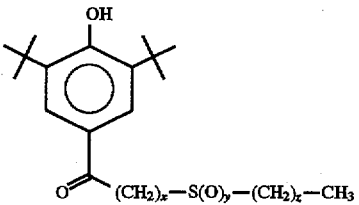

wherein
(a) x is from 1 to 5;
(b) y is from 1 to 2; and
(c) z is from 0 to 5.

Preferably x is from 1 to 3; more preferably from 1 to 2. Preferably z is from 0 to 3; more preferably from 1 to 3. When x is 1 and z is 1, y is preferably 2.

Preferred compounds of the subject invention include those having the above structure with x, y and z as indicated in the following table:

| Compound No. | x | y | z |
| --- | --- | --- | --- |
| 1 | 1 | 2 | 0 |
| 2 | 1 | 1 | 0 |
| 3 | 2 | 1 | 0 |
| 4 | 1 | 1 | 1 |
| 5 | 2 | 2 | 0 |
| 6 | 1 | 2 | 1 |

In order to determine and assess pharmacological activity, testing of the subject compounds in animals is carded out using various assays known to those skilled in the art. The anti-inflammatory activity of the subject compounds can be conveniently demonstrated using an assay designed to test the ability of the subject compounds to antagonize the local edema which is characteristic of the inflammatory response. Examples of such known tests include the rat carrageenan edema test, the oxazolone-induced inflamed mouse ear test, and the mouse arachadonic acid-induced inflamed ear test. Analgesic activity may be tested in art-known models such as the phenylbenzoquinone-induced writhing test in mice, and the Randall & Selitto test in rats. Another useful art-known test is the rat adjuvant arthritis test which is a useful model for assessing anti-inflammatory activity, anti-arthritic and anti-resorptive activity in a chronic, rather than an acute, model.

These and other appropriate tests for pharmacological activity are disclosed and/or referred to in U.S. Pat. No. 4,130,666 issued to Moore on Dec. 19, 1978; U.S. Pat. No. 4,431,656 issued Feb. 14, 1984 to Katsumi, et al.; U.S. Pat. No. 4,440,784 issued to Katsumi, et al. on Apr. 3, 1984; Japanese Patent Application 85/543 15 of Katsumi, et at., published Mar. 28, 1985; European Patent Application No. 0,059,090 of Yamanuchi Pharmaceutical Company Ltd., published Sep. 1, 1982; Opas, E. V., R. J. Bonney & J. L. Humes, "Prostaglandin and Leukotriene Synthesis in Mouse Ears Inflamed by Arachadonic Acid", *The Journal of Investigative Dermatology*, Vol. 84, No. 4 (1985), pp. 253–256; Swingle, K. F., R. L. Bell & G. G. I. Moore, "Antiinflammatory Activity of Antioxidants", *Antiinflammatory and Antirheumatic Drugs*, Vol. III, Chapter 4, K. D. Rainsford, ed., CRC Press, Inc., (1985), pp. 105–126; Adamkiewicz, V. W., W. B. Rice & J. D. McColl, "Antiphlogistic Effect of Trypsin in Normal and in Adrenalectomized Rats", *Canadian Journal of Biochemistry & Physiology*, Vol. 33 (1955), pp. 332–339; Sellye, H., "Further Studies Concerning the Participation of the Adrenal Cortex in the Pathogenesis of Arthritis", *British Medical Journal*, Vol. 2 (1949), pp. 1129–1135; and Winter, C. A., E. A. Risley & G. W. Nuss, "Carrageenan-Induced Edema in Hind Paw of the Rats as an Assay for Antiinflammatory Drugs" *Proceedings of Society of Experimental Biology and Medicine*, Vol. 111 (1962), pp. 544–547; Otterness, I., & M. L. Bliven, "Laboratory Methods for Testing Nonsteroidal Antiinflammatory Drugs", *Nonsteroidal Antiinflammatory Drugs*, Chapter 3, J. G. Lombardino, ed., John Wiley & Sons, Inc. (1985), pp. 111–252. Hitchens, J. T., S. Goldstein, L. Shemano & J. M. Beiler, "Analgesic Effects of Irritants in Three Models of Experimentally-Induced Pain", *Arch. Int. Pharmacodyn.*, Vol. 169, No. 2 (1967) pp. 384–393; Milne, G. M. & T. M. Twomey, "The Analgetic Properties of Piroxicam in Animals and Correlation with Experimentally Determined Plasma Levels", *Agents and Actions*, Vol. 10, No. ½ (1980), pp. 31–37; Randall, L. O. & J. J. Selitto, "A Method for Measurement of Analgesic Activity on Inflamed Tissue", *Arch. Int. Pharmacodyn.*, Vol. 111, No. 4 (1957), pp. 409–419; Winter, C. A. & L. Faltaker, "Nociceptive Thresholds as Affected by Parenteral Administration of Irritants and of Various Antinociceptive Drugs", *J. Pharmacol. Exp. Ther.*, Vol. 148, No. 3 (1965), pp. 373–379; the disclosure of all these references are incorporated herein by reference.

Many anti-inflammatory drugs, particularly non-steroidal anti-inflammatory drugs (NSAIDs) cause undesirable gastrointestinal side effects, especially when dosed perorally; such side effects may include ulcers and erosions. These side effects, which are often asymptomatic, can become serious enough to require hospitalization and can even be lethal. Compounds of the subject invention generally cause fewer such gastrointestinal side effects compared to other NSAIDs, even compared to many other di-tert-butylphenol derivatives. Some compounds of the subject invention are even gastroprotective, protecting the stomach from ulcers and erosions, particularly those caused by ethanol or other NSAIDs.

Certain NSAIDs, including certain di-tert-butylphenol derivatives, when dosed systemically, cause an undesirable increase in systemic levels of certain liver enzymes. Compounds of the subject invention generally cause less of such liver enzyme side effects compared to other di-tert-butylphenol compounds.

Compounds useful in the subject invention can be made using the following general reaction schemes:

(A)

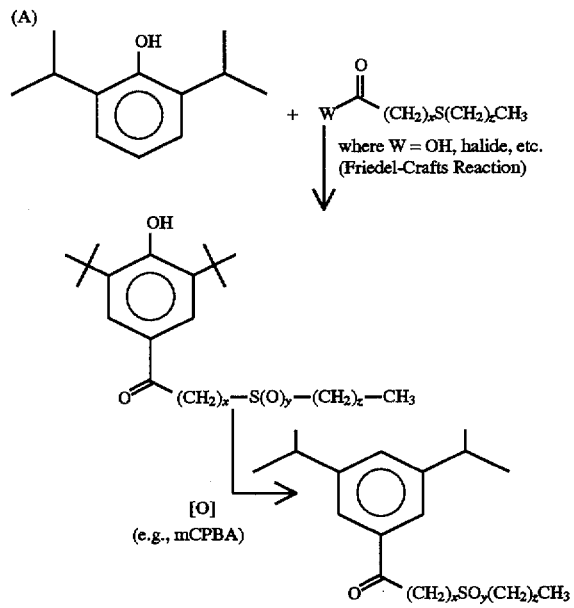

The following non-limiting examples provide further information regarding synthesis of the subject compounds.

EXAMPLE 1

1-(3,5-di-t-butyl-4-hydroxyphenyl)-2-(methylsulfanyl)ethanone 2,6-di-t-butylphenol (1.7680 g, 8.66mmol) is placed in a flame dried RBF, and 2-(methylthio)acetic acid (0.80 mL, 9.19 mmol) is then added. This is then blanketed with argon and TFAA (1.30 mL, 9.20 mmol) is added via syringe at a fast rate. A small amount of CH2C12 is added to aid in mixing. The reaction quickly turns violet and darkens. It is followed by TLC using 10% EtOAc in hexanes. After 5 h, the reaction is carefully poured into 70 mL saturated bicarbonate and extracted with 2 portions of Et2O. The combined organics are washed with brine, filtered through cotton, dried over molecular sieves, then concentrated on a rotavap and dried under vacuum. This gives a white solid which can be crystallized from EtOAc/hexanes to give orange crystals, mp=108.5°–109.5° C.

EXAMPLE 2

1-(3,5-di-t-butyl-4-hydroxyphenyl)-2-(methylsulfinyl)ethanone 1-(3,5-di-t-butyl-4-hydroxyphenyl)-2-(methylsulfanyl) ethanone (15.00 g, 50.94 mmol) is dissolved in CH2Cl2 (100 mL) in a flame-dried flask under argon then cooled in an ice/H2O bath. mCPBA (85%, 10.45 g, 51.47 mmol) is added carefully, generating some gas evolution of H2. The reaction is stirred for 1.75 h while maintaining the bath temperature until the last 20 minutes when the bath is allowed to warm. The reaction is then poured into saturated bicarbonate, separated and extracted with 2× CH2Cl2. The organics are concentrated on a rotavap then dried under vacuum (being careful of foaming). This gives a light tan foam which is purified by flash chromatography on silica with 1.6 L 27.5% acetone in hexanes then 100% acetone. A white solid is obtained which can be crystallized with EtOAc/hexanes with refrigeration to give white crystals, mp=143.6°–144.9° C.

EXAMPLE 3

1-(3,5,-di-t-butyl-4-hydroxyphenyl)-2-(methylsulfonyl)ethanone 1-(3,5-di-t-butyl-4-hydroxyphenyl)-2-(methylsulfanyl) ethanone (2.7422 g, 9.31 mmol) is dissolved in CH2Cl2 (30 mL) in an RBF under argon then cooled in an ice/H2O bath. mCPBA (85%, 4.35 g, 21.4 mmol) is carefully added. A white precipitate forms making stirring difficult so more CH2Cl2 is added. The reaction is stirred overnight, allowing the cooling bath to warm. The next morning, it is transferred to a separatory funnel, diluted to ~125 mL and washed with 2× dilute sodium bisulfite then 2× 0.5N bicarbonate. The combined organics are filtered through cotton, dried over mol sieves, concentrated on a rotavap then dried under vacuum being careful of foaming. This gives a yellow foam which can be crystallized from EtOAc/hexanes to give white crystals, mp=138.6°–139.5° C.

EXAMPLE 4

1-(3,5-di-t-butyl-4-hydroxyphenyl)-3-(methylsulfinyl)propan-1-one

This material is obtained from 1-(3,5,-di-t-butyl-4-hydroxyphenyl)-3-(methylsulfanyl)propan-1-one following the (method of 1-(3,5-di-t-butyl-4-hydroxyphenyl)-2-(methylsulfinyl)ethanone). The product is purified by flash chromatography with 30% acetone in hexanes and recrystallized from EtOAc/hexanes, mp=158.8°–159.5° C.

EXAMPLE 5

1-(3,5-di-t-butyl-4-hydroxyphenyl)-2-(ethylsulfinyl)ethanone

This material is obtained from 1-(3,5-di-t-butyl-4-hydroxyphenyl)-2-(ethylsulfanyl)ethanone following (the method of 1-(3,5,-di-t-butyl-4-hydroxyphenyl)-2-(methylsulfinyl)ethanone). The material is purified by flash chromatography with 25% acetone in hexanes followed by crystallization from EtOAc/hexanes with refrigeration giving white crystals, mp=133°–134° C.

EXAMPLE 6

1-(3,5-di-t-butyl-4-hydroxyphenyl)-3-(methylsulfonyl)propan-1-one

This material was prepared from 1-(3,5,-di-t-butyl-4-hydroxyphenyl)-3-(methylsulfanyl)propan-1-one following (the method of 1-(3,5,-di-t-butyl-4-hydroxyphenyl)-2-(methylsulfanyl)propan-1-one). A flash chromatography with 100% acetone followed by recrystallization from EtOAc/pentane gives a white fluffy solid, mp=167.9°–168.5° C.

EXAMPLE 7

1-(3,5-di-t-butyl-4-hydroxyphenyl)-2-(ethylsulfonyl)ethanone

This material is prepared from impure 1-(3,5-di-t-butyl-4-hydroxyphenyl)-2-(ethylsulfanyl)ethanone (following the method of 1-(3,5,-di-t-butyl-4-hydroxyphenyl)-2-(methylsulfonyl)ethanone). Crystallization (of the crude product) from EtOAc/hexanes followed by a second crystallization then a flash chromatography with EtOAc followed by a third crystallization with refrigeration gives white crystals, mp=119.5°–120.5° C.

Compositions of the subject invention comprise a safe and effective amount of the subject compounds, and a pharmaceutically-acceptable carrier. As used herein, "safe and effective amount" means an amount of a compound sufficient to significantly induce a positive modification in the condition to be treated, but low enough to avoid serious side effects (at a reasonable benefit/risk ratio), within the scope of sound medical judgment. A safe and effective amount of a compound will vary with the particular condition being treated, the age and physical condition of the patient being treated, the severity of the condition, the duration of the treatment, the nature of concurrent therapy, the particular pharmaceutically-acceptable carrier utilized, and like factors within the knowledge and expertise of the attending physician.

Compositions of the subject invention preferably comprise from about 0.1% to about 99.9% by weight of a compound, more preferably from about 20% to about 80%, and most preferably from about 40% to about 70%.

In addition to the compound, the compositions of the subject invention contain a pharmaceutically-acceptable carrier. The term "pharmaceutically-acceptable carrier", as used herein, means one or more compatible solid or liquid filler diluents or encapsulating substances which are suitable for administration to a human or lower animal. The term "compatible", as used herein, means that the components of the composition are capable of being commingled with the subject compound, and with each other, in a manner such that there is no interaction which would substantially reduce the pharmaceutical efficacy of the composition under ordinary use situations. Pharmaceutically-acceptable carriers must, of course, be of sufficiently high purity and sufficiently low toxicity to render them suitable for administration to the human or lower animal being treated.

Some examples of substances which can serve as pharmaceutically-acceptable carriers or components thereof are sugars, such as lactose, glucose and sucrose; starches, such as cornstarch and potato starch; cellulose and its derivatives, such as sodium carboxymethyl cellulose, ethyl cellulose, cellulose acetate; powdered tragacanth; malt; gelatin; talc; solid lubricants, such as stearic acid, magnesium stearate; calcium sulfate; triglycerides and derivatives; vegetable oils, such as peanut oil, cottonseed oil, sesame oil, olive oil, corn oil and oil of theobroma; polyols such as propylene glycol, glycerin, sorbitol, mannitol, and polyethylene glycol; alginic acid; emulsifiers, such as the Tweens®; wetting agents such as sodium lauryl sulfate; coloring agents; flavoring agents, excipients; tableting agents; stabilizers; antioxidants; preservatives; pyrogen-free water; isotonic saline; and phosphate buffer solutions.

The choice of a pharmaceutically-acceptable carrier to be used in conjunction with a subject compound is basically determined by the way the compound is to be administered.

If the subject compound is to be injected, it is preferably injected non-intravenously; the preferred pharmaceutically-acceptable carrier is sterile, physiological saline, with blood compatible suspending agent, the pH of which has been adjusted to about 7.4. Such injectable compositions preferably comprise from about 1% to about 50% of the subject compound, more preferably from about 5% to about 25%, also preferably from about 10 mg to about 600 mg of the subject compound per dose.

Suitable pharmaceutically-acceptable carriers for topical application include those suited for use in lotions, creams, gels and the like. Topical compositions preferably contain from about 1% to about 50% of an emollient, more preferably from about 5% to about 25% of an emollient. Such topical compositions preferably comprise from about 0.1% to about 50%, of the subject compound, more preferably from about 0.5% to about 10%, also preferably from about 5 mg to about 3500 mg per dose.

The preferred mode of administering the subject compound is perorally. The preferred unit dosage form is therefore tablets, capsules and the like, comprising a safe and effective amount of the compound, which is preferably from about 5 mg to about 3500 mg, more preferably from about 10 mg to about 1000 mg, and most preferably from about 25 mg to about 600 mg. The pharmaceutically-acceptable carriers suitable for the preparation of unit dosage forms for oral administration are well-known in the art. Their selection will depend on secondary considerations like taste, cost, and shelf stability, which are not critical for the purposes of the subject invention, and can be made without difficulty by a person skilled in the art.

Many of the subject compounds are hydrophobic. If it is desired to provide an aqueous-based composition or a composition soluble in or miscible with aqueous media, a solubilizing agent may be included in the composition. Non-limiting examples of such solubilizing agents include polyethylene glycol, propylene glycol, ethanol, and polyoxyethylene (35) castor oil.

Particularly preferred oral composition carriers suitable for compositions of the subject invention are disclosed in U.S. Pat. Nos. 5,189,066 of Kelm & Bruns, issued Feb. 23, 1993, entitled "Pharmaceutical Compositions of Tebufelone", and 5,281,420 of Kelm & Dobrozsi, issued Jan. 25, 1994, entitled "Solid Dispersion Compositions of Tebufelone", hereby incorporated herein by reference.

The preferred mode of administration of the subject compounds is peroral, but other known methods of administration are contemplated as well, e.g., dermatomucosally (for example, derreally, rectally and the like), and parenterally (for example, by subcutaneous injection, intramuscular injection, intraarticular injection, intravenous injection and the like). Ocular administration and inhalation are also included. Thus specific modes of administration include, without limitation, peroral, transdermal, mucosal, sublingual, intranasal, intramuscular, intravenous, intraperitoneal, subcutaneous, and topical administration.

Preferred doses of the subject compounds range from about 0.2 mg/kg to about 70 mg/kg, more preferably from about 0.5 mg/kg to about 12 mg/kg. Preferred injectable doses comprise from about 0.1 mg/kg to about 10 mg/kg of the subject compound. Preferred topical doses comprise from about 1 mg/cm2 to about 200 mg/cm2 of the subject compound applied to the skin surface. Preferred peroral doses comprise from about 0.5 mg/kg to about 50 mg/kg, more preferably from about 1 mg/kg to about 10 mg/kg, of the subject compound. Such doses are preferably administered from about once to about six times daily, more preferably from about twice to about four times daily. Such daily doses are preferably administered for at least one week, also preferably for at least two weeks, also preferably at least one month, also preferably for at least 2 months, also preferably for at least 6 months, 1 year, 2 years, or more.

The following non-limiting examples illustrate the subject invention.

EXAMPLE A

Pharmaceutical compositions in the form of tablets are prepared by conventional methods, such as mixing and direct compaction, formulated as follows:

| Ingredient | Quantity (mg per tablet) |
| --- | --- |
| Compound 1 | 200 |
| Microcrystalline Cellulose | 100 |
| Sodium Starch Glycollate | 30 |
| Magnesium Stearate | 3 |

When administered orally two times daily, the above composition significantly reduces the inflammation in a patient suffering from rheumatoid arthritis. A significant benefit is also achieved by twice daily administration of this composition to a patient suffering from osteoarthritis.

EXAMPLE B

A pharmaceutical composition in capsule form is prepared by conventional methods, formulated as follows:

| Ingredient | Quantity (mg per capsule) |
| --- | --- |
| Compound 2 | 200 |
| Lactose | To fill to volume of capsule |

The above capsule administered orally once a day substantially reduces the symptomology of a patient afflicted with rheumatoid arthritis or osteoarthritis.

EXAMPLE C

A oral solid dosage pharmaceutical composition is prepared by conventional methods, formulated as follows:

| Ingredient | Quantity (% weight) |
| --- | --- |
| Compound 6 | 20% |
| Pluronic F108 | 40% |
| Tween ® | 40% |

EXAMPLE D

An oral solid dosage pharmaceutical composition is prepared by conventional methods, formulated as follows:

| Ingredient | Quantity (% weight) |
|---|---|
| Compound 6 | 50% |
| Triglycerides and Derivatives | 45% |
| Cremaphor EL | 5% |

Another aspect of the subject invention is methods for treating or preventing diseases characterized by intimation by administering a safe and effective amount of a subject compound to a human or lower animal in need of such treatment. The term "diseases characterized by inflammation", as used herein, means conditions which are known to involve inflammation, and may include conditions such as arthritis (e.g., rheumatoid arthritis, osteoarthritis, psoriatic arthritis, juvenile arthritis, Reiter's syndrome, infectious arthritis, and ankylosing spondylitis, systemic lupus, erythematosus and gout), as well as the presence of inflammation whether or not it is associated with an identifiable disease. Diseases characterized by inflammation further may include inflammation in the oral cavity (e.g., inflammation associated with gingivitis or periodontal disease); intimation in the gastrointestinal tract, (e.g., intimation associated with ulcers and irritable bowel disease); inflammation associated with dermatological diseases (e.g., psoriasis, acne, and other skin inflammation); inflammation associated with the respiratory tract (e.g., asthma, bronchitis, and allergies); and intimation in the central nervous system (e.g., Alzheimer's disease).

Another aspect of the subject invention is methods for treating or preventing pain by administering a safe and effective amount of a subject compound to a human or lower animal in need of such treatment. Pain which can be treated or prevented by administering the subject compounds may include peripheral pain, menstrual pain, dental pain, and lower back pain.

Another aspect of the subject invention is methods for protecting against free radical damage resulting from oxidative stress and ischemic conditions by administering a safe and effective amount of a subject compound to a human or lower animal in need of such treatment. Such treatment may include protecting against ischemic heart disease, atherosclerosis, stroke, and ischemic cell damage of heart.

Another aspect of the subject invention is methods for treating or preventing gastric or duodenal ulcers or erosions by administering a safe and effective amount of a subject compound to a human or lower animal in need of such treatment. In particular, such ulcers or erosions caused by ethanol or non-steroidal antiinflammatory drugs (NSAIDs) can be treated and/or prevented by administration of preferred subject compounds.

Appropriate tests for determining the gastrointestinal safety or gastroprotective or gastric healing properties of the subject compounds are known.

Methods for determining acute gastrointestinal safety are disclosed and/or referred to in the following references: Unangst, P. C., G. P. Shrum, D. T. Connor, R. D. Dyer, and D. J. Schrier, "Novel 1,2,4-Oxadiazoles and 1,2,4-Thiadiazoles as Dual 5-Lipoxygenase and Cyclooxygenase Inhibitors", *J. Med. Chem.*, Vol. 35 (1992), pp. 3691–3698; and Segawa, Y, O. Ohya, T. Abe, T. Omata, et at., "Antiinflammatory, Analgesic, and Antipyretic Effects and Gastrointestinal Toxicity of the New Anti-inflammatory Drug N-{3-[3-(piperidinylmethyl)phenoxy]propyl}-carbamoylmethylthio]ethyl 1-(p-chlorobenzoyl) 5-Methoxy-2methyl-3-indolylacetate", *Arzneim.-Forsch./ Drug Res.*, Vol. 42 (1992), pp. 954–992. In the methods disclosed therein, stomachs of the animals are typically examined two hours after dosing a compound.

Methods for determining subchronic gastrointestinal safety are disclosed and/or referred to in the following references: Melarange, R., C. Gentry, et al., "Antiinflammatory and Gastrointestinal Effects of Nabumetone or Its Active Metabolite, 6-Methoxy-2-naphthylacetic Acid (6MNA)", *Dig. Dis. Sci.*, Vol. 37 (1992), pp. 1847–1852; and Wong, S., S. J. Lee, et al., "Antiarthritic Profile of BF-389—A Novel Anti-inflammatory Agent With Low Ulcerogenic Liability", *Agents Actions*, Vol. 37 (1992), pp. 90–91.

Methods for determining acute gastroprotection are disclosed and/or referred to in the following reference: Playford, R. J., D. A. Versey, S. Haldane, M. R. Alison, and J. Calan, "Dose-dependent Effects of Fentanyl on Indomethacin-induced Gastric Damage", *Digestion*, Vol. 49 (1991), pp. 198–203. In the method disclosed therein, female Lewis rats (130–175 g) are dosed perorally with the subject compound (40 mg/kg b.i.d.) or vehicle at 2 hours and immediately before administration of a gastric damaging dose of indomethacin. The rats are sacrificed 4 hours later by $CO_2$ asphyxiation. Gastric corpus damage (millimeters of hemorrhagic lesions) is measured by digitized imaging.

While particular embodiments of the subject invention have been described, it would be obvious to those skilled in the art that various changes and modifications to the compositions disclosed herein can be made without departing from the spirit and scope of the invention. It is intended to cover, in the appended claims, all such modifications that are within the scope of this invention.

What is claimed is:

1. A compound having the structure:

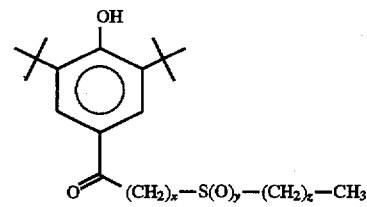

wherein
 (a) x is from 1 to 5;
 (b) y is from 1 to 2; and
 (c) z is from 0 to 5;
where when both x and y are one, z is not 0.

2. The compound of claim 1 wherein x is from 1 to 3.
3. The compound of claim 1 wherein x is from 1 to 2.
4. The compound of claim 2 wherein z is from 0 to 3.
5. The compound of claim 4 wherein x is 1 to 2.
6. The compound of claim 5 wherein z is 0 to 1.
7. The compound of claim 6 wherein y is 1.
8. The compound of claim 6 wherein y is 2.
9. The compound of claim 8 wherein x is 1.
10. The compound of claim 8 wherein x is 2.
11. The compound of claim 9 wherein z is 0.
12. The compound of claim 9 wherein z is 1.
13. A pharmaceutical composition comprising:
 (a) a safe and effective amount of the compound of any claims 1, 5, and 12; and
 (b) a pharmaceutically-acceptable carrier.
14. A method of treating intimation or pain comprising the peroral administration of a safe and effective mount of the compound of any of claims 1, 5, and 10.

15. A method of treating inflammation or pain comprising the peroral administration of a safe and effective amount of a pharmaceutical composition comprising a compound having the structure:
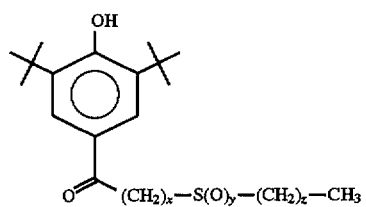
wherein
(a) x is from 1 to 5;
(b) y is from 1 to 2; and
(c) z is from 0 to 5; and
a pharmaceutically acceptable carrier.
* * * * *

UNITED STATES PATENT AND TRADEMARK OFFICE
CERTIFICATE OF CORRECTION

PATENT NO. : 5,684,204
DATED : November 4, 1997
INVENTOR(S) : Randall Stryker Matthews It is certified that error appears in the above-identified patent and that said Letters Patent is hereby corrected as shown below:

Column 10, line 65, "intimation" should read –inflammation--

Column 10, line 66, "mount" should read –amount--.

Signed and Sealed this

Nineteenth Day of May, 1998

*Attest:*

BRUCE LEHMAN

*Attesting Officer*     *Commissioner of Patents and Trademarks*